Figure 1:
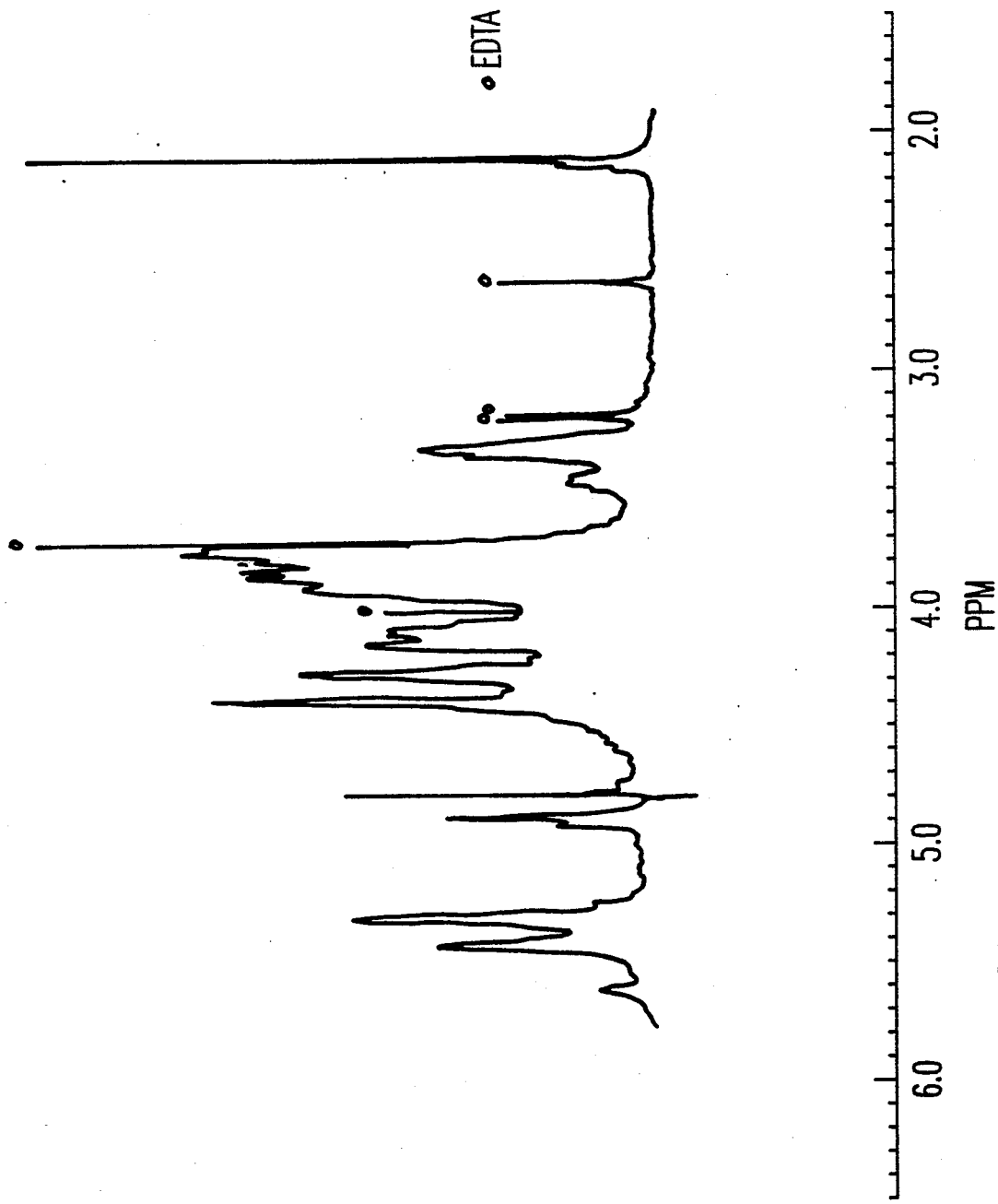

United States Patent [19]

Casu et al.

[11] Patent Number: 5,110,918
[45] Date of Patent: May 5, 1992

[54] PROCESS FOR PREPARING EDTA-FREE HEPARINS, HEPARIN FRACTIONS AND FRAGMENTS

[75] Inventors: Benito Casu; Annamaria Naggi; Pasqua Oreste; Giangiacomo Torri; Giorgio Zoppetti; Giancarlo Sportoletti; Francesco De Santis, all of Milan, Italy

[73] Assignee: Sanofi S.A., Paris, France

[21] Appl. No.: 587,605

[22] Filed: Sep. 24, 1990

Related U.S. Application Data

[63] Continuation of Ser. No. 364,576, Jun. 8, 1989, abandoned, which is a continuation of Ser. No. 50,287, May 14, 1987, abandoned.

[30] Foreign Application Priority Data

May 16, 1986 [IT] Italy .............................. 20462 A/86
Oct. 3, 1986 [IT] Italy .............................. 21901 A/86

[51] Int. Cl.$^5$ .................... A61K 31/725; C08B 37/10
[52] U.S. Cl. ........................................ 536/21; 514/56
[58] Field of Search ............................. 514/56; 536/21

[56] References Cited

U.S. PATENT DOCUMENTS 4,652,555  3/1987  Goulay et al. ................... 514/56
4,692,435  9/1987  Lormeau et al. ................ 514/56

FOREIGN PATENT DOCUMENTS 3244214  5/1984  Fed. Rep. of Germany ........ 536/21
2027728  12/1980  United Kingdom ................ 514/56
2071127  9/1981  United Kingdom ................ 514/56

OTHER PUBLICATIONS

Heparin—Past, Present and Future by Erwin Coyne, pp. 10-17, copyright 1981 by Elsevier North Holland, Inc.
The United States Pharmacopeia, Jan. 1985, pp. 480-483.
British Pharmacopoeia, 1988, pp. 282-283.
Pharmacopee Europeenne, 1984, pp. 332 through 332-4, 333 through 333-5.

Primary Examiner—Douglas W. Robinson
Assistant Examiner—Jean Witz
Attorney, Agent, or Firm—Oblon, Spivak, McClelland, Maier & Neustadt

[57] ABSTRACT

Heparins, heparin fractions or fragments, optionally salified with pharmaceutically acceptable cations, having molecular weight ranging from 1.000 to 30.000 D, characterized by an EDTA content lower than 0.1%, by the absence, in the $^1$H—NMR spectra, of the signals due to EDTA between 2.50 and 4.00 p.p.m. and substantially free from bleeding effect and optionally free from signals, in the $^{13}$C—NMR spectrum, from 80 to 86 ppm.

2 Claims, 10 Drawing Sheets

PROCESS FOR PREPARING EDTA-FREE HEPARINS, HEPARIN FRACTIONS AND FRAGMENTS

This application is a continuation of application Ser. No. 07/364,576, filed on Jun. 8, 1989, now abandoned, which is a continuation of Ser. No. 07/050,287, filed on May 14, 1987, now abandoned.

The present invention refers to purified heparins, purified heparin fractions and fragments, processes for the preparation thereof and pharmaceutical compositions containing them.

Heparin is a biopolymer extracted from tissues of different kind: bovine or porcine, intestinal mucosa, lung etc.

The extraction procedures have constantly been improved leading to heparins having higher and higher biological activity (measured as anticoagulant activity, APTT or anti-Xa activity) related to an higher purity of the substance.

Chemically, heparin, its fractions and fragments (LMW-Hep)(obtained from heparin by physical fractionation or chemical and enzymatic degradation) are sulphated glycosaminoglycans wherein the main building blocks are: L-iduronic 2-sulphate acid and N,6 disulphate glucosamine. Sometimes, the uronic moiety consists of D-glucuronic acid or L-uronic acid (both unsulphated), whereas the aminosugar may be N-acetylated (rather than N-sulfated), or undersulphated (at the oxygen in 6), or oversulphated (at the oxygen in 3).

The glycosidic bonds between the different units are always 1→4, with α configuration. The different molecules differ in molecular weight, i.e. in the number of polycondensed units. The molecular weights (considering both fragments and fractions) range from about 1,000 to about 30,000 D.

Being a mixture having polydispersed molecular weight, the chemico-physical characteristics are the mean values of the mixture.

Even though with some differences related to the extraction source (tissue), there is a general homogenity between the different commercial preparations concerning the various chemico-physical characteristics, such as electrophoretic pattern, the sulphur and nitrogen content and the biological ones, such as, for instance, the anticoagulant activity expressed as international units U.S.P./mg (U.I./mg).

The use of either $^{13}C$ or $^{1}H$-Nuclear Magnetic Resonance gives spectra in complete agreement with the structure of the various moieties involved and substantially homogeneous for each commercial batch.

In the $^{13}C$—N.M.R. spectrum recorded between 20 and 180 p.p.m., there are many signals which have been certainly attributed to heparin whereas for other signals it has been not yet possible to give an attribution. This is the case of the signals between 80 and 86 p.p.m. and of different signals between 55 and 70 p.p.m., always present (with different intensity degree) in all the heparin samples, even in those with the highest purification degree, obtainable by the usually available industrial methods.

While the main heparin signals in the proton spectra are well known, some other extra-signals (ex. those between 2.5 and 4.00 p.p.m.) have not been yet certainly assigned. From the biological point of view, the heparin shows interesting pharmacological activities, namely anticoagulant, antilipaemic and anti-thrombotic activity, useful in human therapy in those conditions where an hypercoagulability and hyperthrombotic risk exists, such as the post-surgical conditions or the deep venous thrombosis.

A limit to the therapeutic use of heparin (in its different salt forms: sodium, calcium etc.) or of its fractions or fragments is however the so called "bleeding", i.e. an anomalous blood loss not related (in a constant way) to the anticoagulant activity corresponding to a known amount of heparin (or fractions or fragments) administered to the patient; said bleeding occurs often both in man and in other mammals, even after single administration.

According to what is presently known, said phenomenon is ascribed to the heparin nature itself, because heparin is presumed to interfere, in some patients, with unknown mechanisms of primary haemostasis or to induce thrombocytopenia.

It has now been found that the signals between 55 and 70 p.p.m. in the $^{13}C$—NMR and from 2.50 to 4.00 p.p.m. in the $^{1}H$-NMR spectrum, not related to heparin-like structures, are partially due to the presence of a foreign contaminant, in relevant amounts.

This is particularly noticeable by means of the signals at the $^{1}H$—NMR.

Said component, always present in all the industrial preparations, also those purified to the maximum obtainable grade according to the presently used methods, in amounts ranging from 0.2 to 5% by weight, turned out to be ethylendiaminotetraacetic acid (EDTA), present in different forms, including (sodium or calcium) EDTA in free form (signals at 2.61, 3.16, 3.18 p.p.m.) and partially interacting with the heparin-like structures (signals at 3.25, 3.64, 3.71, 3.99 p.p.m. shifted of 0.53–1.1 p.p.m. in comparison to those of free EDTA: said shift is reasonably ascribable to said interaction EDTA-Heparin).

Quantitatively, the reciprocal ratios between said impurity forms (free or interacting) vary from batch to batch.

It has been moreover surprisingly found that the elimination of EDTA and, as a consequence, of the above reported signals in the NMR spectra, yield heparins or heparin fractions free from bleeding effect.

Infact, even if it is known that EDTA is endowed with anticoagulant activity, said activity occurs only at doses 20 to 30 times higher than those attainable by the administration of heparins wherein EDTA is present as contaminant at the maximum concentration.

Thus, if from one side the bleeding effect of said heparins cannot simply be ascribed to the presence of small or very small amounts of EDTA, on the other side, it is surprising that the removal of EDTA traces yields heparins completely devoid of bleeding effect.

A first object of the present invention is therefore provided by heparins, heparin fractions or fragments, characterized by the absence of the above cited signals in the $^{1}H$ and $^{13}C$—NMR.

Said heparins are characterized by an EDTA content lower than 0.1%, preferably lower than 0.01% and even more preferably free from EDTA and moreover do not exhibit bleeding effect, both after single and repeated administration.

The corresponding sodium, calcium, magnesium salts or with other pharmaceutically acceptable cations are also included within the scope of the invention.

The compounds of the present invention, because of the complete absence of bleeding effect, offer a wider safety of treatment, even after repeated administrations, in comparison with similar compounds up to now studied.

A further object of the invention is therefore provided by pharmaceutical compositions containing as the active principle the compounds of the invention or the salts thereof.

Preferred administration forms are those usually used for heparins and derivatives: vials for intravenous or intramuscolar administration, creams, ointments and also forms suited for the oral administration.

Also the dosages and the treatment schedules are substantially identical to those up to now used for the known compounds, not devoid of bleeding effect.

Still a further object of the invention is provided by the purification and preparation methods of the compounds of the invention.

According to a first method, an aqueous solution of heparin or fragment or fractions thereof, having a concentration ranging fro 0.5 to 30% w/v, is subjected to a series of dialysis and/or diafiltrations on membranes having suitable cut-off values (generally from 500 to 10.000 D, preferably from 500 to 1.000 D), optionally in the presence of NaCl or other highly ionizable salt.

Preferred membranes consist of polyfluorinated polymer (Teflon ®), polysulphone or polyacetate.

Alternatively, aqueous solutions of heparin of different kinds are subjected to precipitation by means of suitable organic solvents, such as methanol, ethanol or acetone, using solvent/water ratio ranging from 0.5/1 to 2/1.

Heparins of different kinds may also be subjected to extractions with suitable aqueous mixtures of organic solvents such as methanol, ethanol, isopropanol, acetone or dioxane having a water content ranging from 23 to 30% (v/v), at temperature from 5° to 20° C. for periods ranging from 5 to 20 minutes, under constant stirring.

The determination of the average molecular weight is carried out by gel-filtration on polyacrylamide gel column (F. A. Johnson, B. Nulloy—Carb. Res., 51, 119, 1976). The biological assay is expressed in U.S.P. international units/mg.

The bleeding time is evaluated in the rat by:

1) Tail transection test (E. Dyana et al., Thromb. Res., 48, 108, 1982). Said test is considered as an in vivo clotting test. It is measured in seconds.

2) Template. Said test reflects primary hemostasis (J. Pangrazzi et al., Biochem. Pharmacol., 34, 3305, 1985). It is measured in seconds.

A possible increase in bleeding time in the first test reflects, "in vivo", the anticoagulant activity of the administered substance. Said activity is expressed "in vitro" by the anticoagulant titer according to the United States Pharmacopeia. An increase in bleeding time in the second test cannot be related to the anticoagulant activity. A substance could even have no anticoagulant activity as U.I./mg but it could eventually induce an increase of the bleeding times in the template test because able to interfere on the regulation of the primary hemostasis, which is able to induce bleeding.

In other words, an increase of bleeding time in the tail transection mainly shows an anticoagulant activity, whereas that obtained in the template test shows a bleeding activity.

In both tests male Sprague-Dawley rats, weighing about 250 g have been used. The products were administered by venous route in sterile and pyrogen-free saline solution at the dose of 0.75 mg/kg, using saline as reference treatment. The bleeding times are reported in seconds.

The experimental groups for each test and each substance consisted of 10 animals.

The standard reference values (controls) obtained by administering only saline solution (0.1 ml/100g body weight) in both tests, were on the average:

Tail transection : 200±16 sec.
Template : 102±4 sec.

EXAMPLE 1

A 2% solution (w/v) of commercial sodium heparin, characterized by the $^1$H—NMR spectrum reported in FIG. 1, wherein the signals at 2.61, 3.16, 3.18, 3.71, 3.99 p.p.m. are evident, by an average molecular weight of 11.000 D and anticoagulant activity of 168 U.I./mg, was subjected to dialysis in a cellulose bag, cut-off 3.500 D, versus distilled water for 24 hours. The content of the dialysis bag was collected by lyophilization. The lyophilized product was then subjected to the $^1$H—NMR analysis and exhibited the spectrum shown in FIG. 2, wherein the absence of the above listed signals is evident. The solution containig the diffusate, after concentration under vacuum, was lyophilized. The lyophilized product was submitted to $^1$H—NMR analysis, after adjusting pH to about 7 by addition of HCl, and showed the spectrum reported in FIG. 3. The signals that were present in it at 2.61, 3.16, 3.18, 3.99 p.p.m. correspond to those present in the original compound; the signal at 3.64 p.p.m. is equivalent to the signal at 3.71 p.p.m. of FIG. 1; moreover, since they are no longer covered by heparin signals, the peaks at 3.71 and 3.25 p.p.m. are evident.

Figure 3:
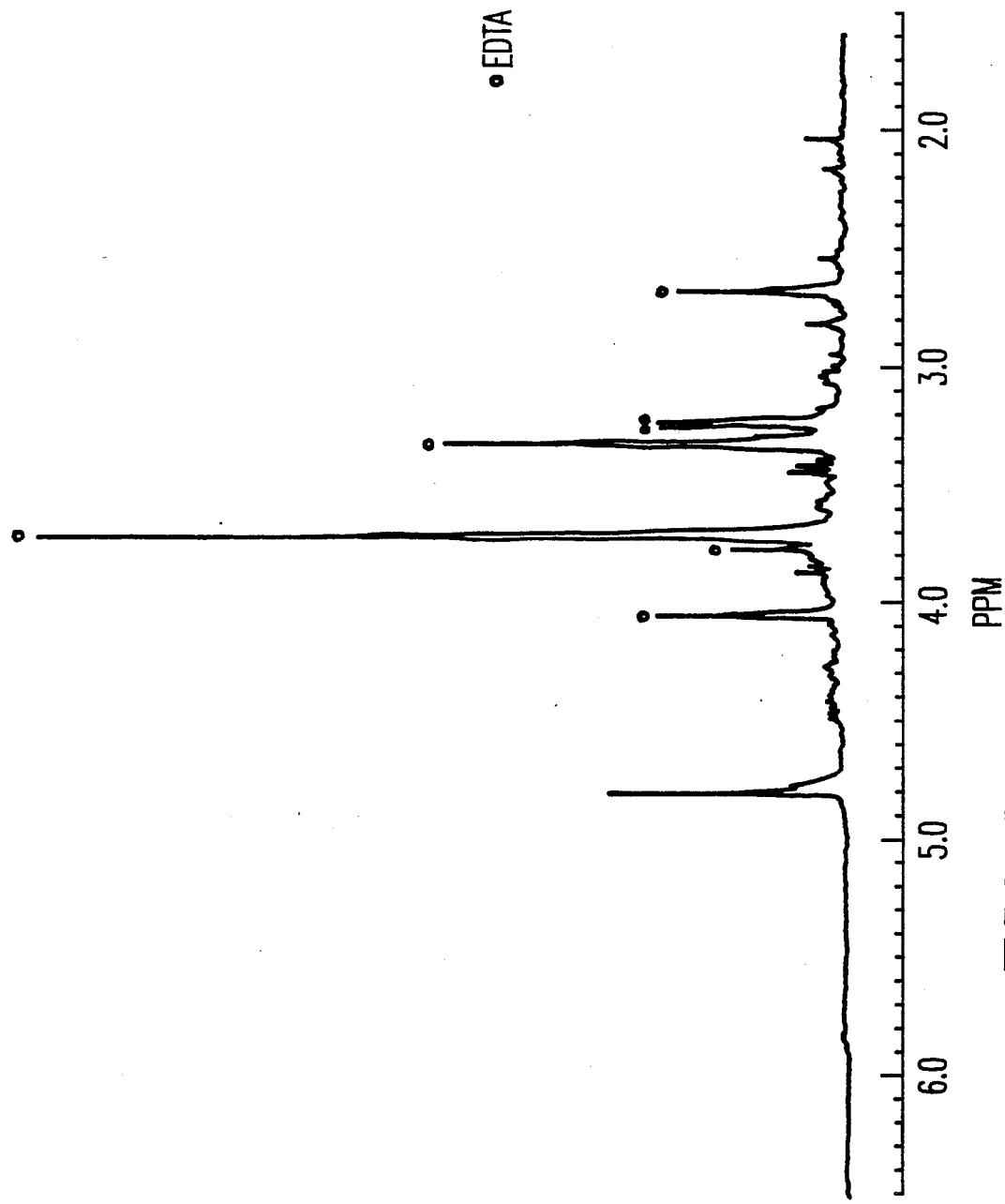

By adding the solution of the diffusate sample an excess of $CaCl_2$, the $^1$H—NMR spectrum showed in FIG. 3 undergoes a remarkable change, with the disappearance of the signal$ at 3.25-3.64-3.71-3.99 p.p.m. The recording is reported in FIG. 4. The signals of this spectrum can be inequivocably assigned to EDTA in calcium form.

On the basis of what reported above, all the signals reported in FIG. 3 (that, therefore, are also present in the initial heparin sample) can be undoubtedly assigned to EDTA. This compound is present in the initial sample in different forms, as shown by the various signals. These forms are both sodium EDTA and EDTA complexed with different cations (that are present as impurities), for example with calcium. Furthermore, these forms can interact with the heparin structures, with a consequent shift of some signals.

In order to dose the total quantity of EDTA in the initial sample, the $^1$H—NMR spectrum of the sample itself was recorded in the presence of an excess of $CaCl_2$. From the integration of the signal at 2.61 p.p.m. and in comparison with an inner standard of 0.01% t-butanol, the total amount of EDTA was calculated as 4.2% in weight.

The heparin sample recovered from dialysis, after lyophilization, showed an anticoagulant activity of 170 U.I./mg, whereas the residue of lyophilization of the dialysis waters showed virtually no anticoagulant activity.

Initial sodium heparin :
Tail transection : 435
Template : 265

The percent deviations, in comparison with the physiologic values, induced by the administration of the sample, are as follows:

Tail transection : +96%
Template : +160%

Whereas the first change can be attributed to the administration of 126 U.I./kg of anticoagulant activity, the abnormal increase of time in the second test cannot be related to this anticoagulant activity (bleeding effect).

Sodium heparin purified by dialysis:
Tail transection : 427
Template : 109

The percent increases, in relation with saline solution, turn out to be +114% for the former and +5% for the latter, the former being in agreement with the administration of about 127 U.I./kg whereas the latter is not significant, since it falls within the method's error.

Sample recovered from the dialysis waters: In both tests the sample did not give values that were significantly different from the values obtained with saline solution.

EXAMPLE 2

A 10% (p/v) solution of commercial sodium heparin, of a different origin than the heparin of example 1, characterized by an average molecular weight of 13.000 D and by an anticoagulant activity of 167 U.I./mg, was submitted to diafiltration, consisting in continuously eluting the solution on a 600 D cutoff polyacetate membrane, keeping constant the volume of the solution, by addition of distilled water in an amount equal to the volume of the obtained diffusate. The operation continued until the diffusate volume reached a value 5 times higher than the initial volume of heparin (in other experiments this volume reached values ranging from 1 to 10 times the initial volume). The recovery of heparin was carried out by lyophilization, and the diffusate waters were also lyophilized.

Figure 5:
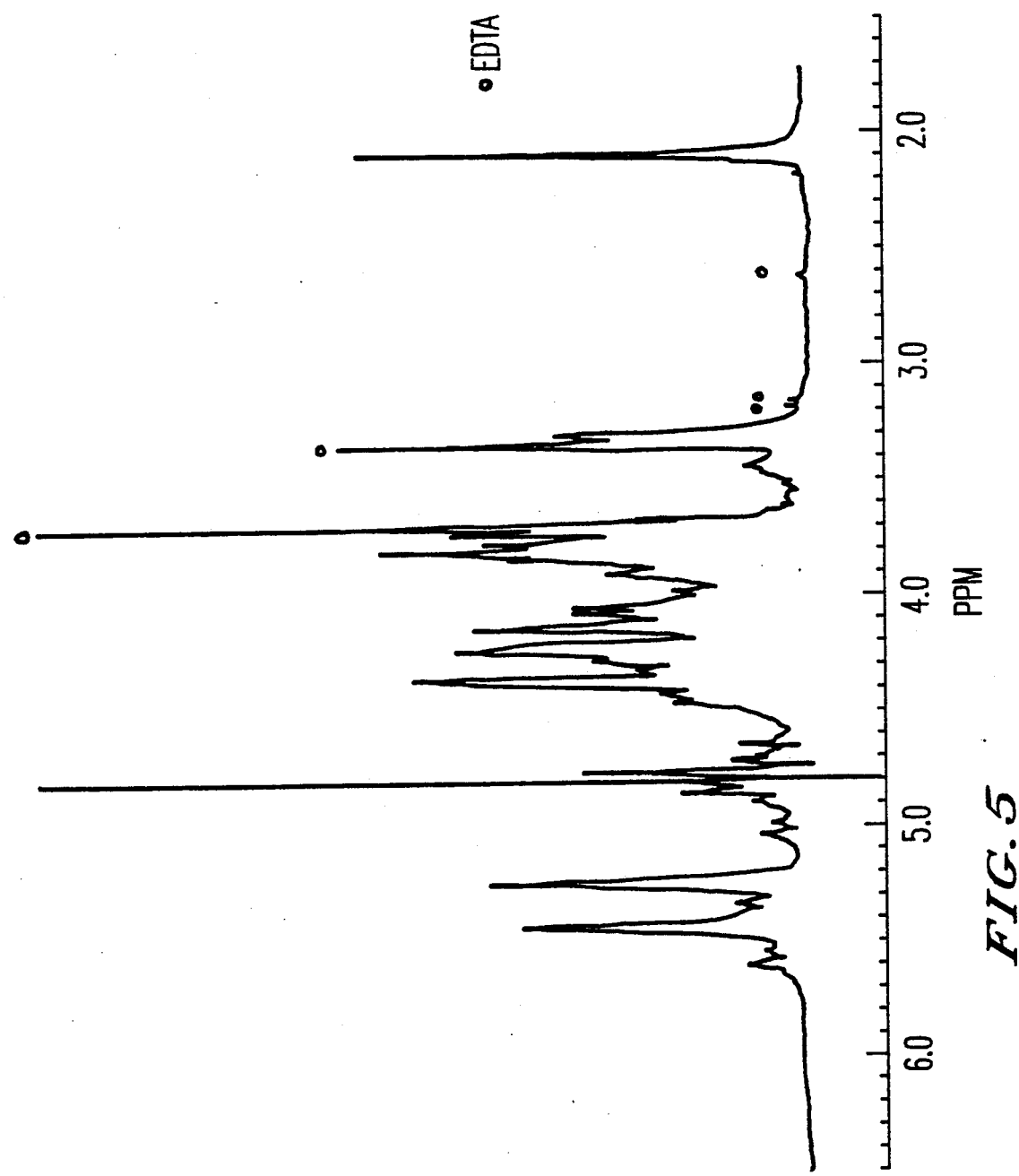

FIG. 5 shows the $^1$H—NMR spectrum of the starting heparin, in which the signals at 2.61-3.16-3.18 p.p.m. proved to be scarcely intense, whereas the signals at 3.35 and 3.99 p.p.m. proved to be very intense. This indicates that EDTA is mainly in form of sodium salt (few calcium impurities or other cations). The purified sample showed an $^1$H—NMR spectrum equal to the spectrum reported in picture 2. Its anticoagulant activity was 165 U.I./mg.

Figure 4:
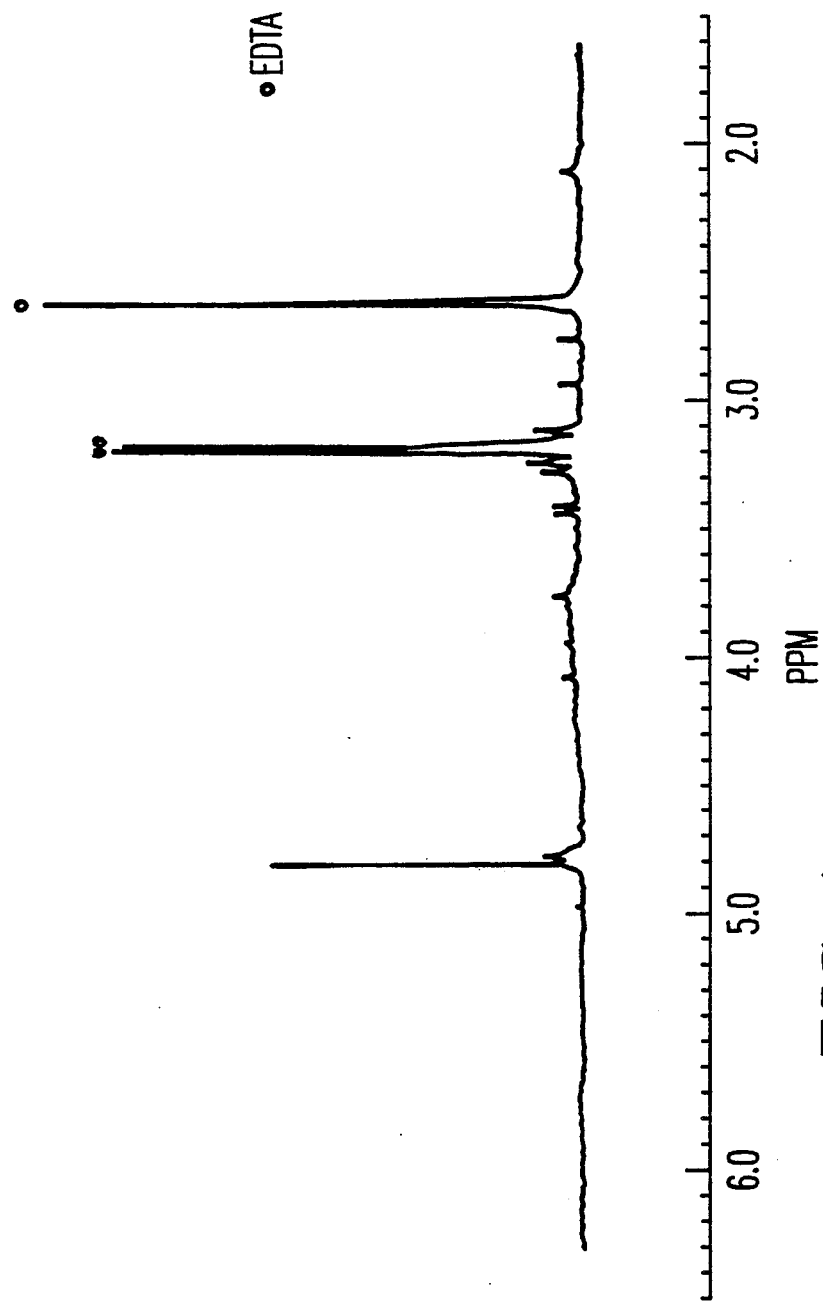

The lyophilization residue of the diffusate shows $^1$H—NHR behavior superimposable to what described in example 1 and illustrated in FIGS. 3 and 4.

The total amount of EDTA in the starting heparin—ascertained by means of the integration of the signal at 2.61 p.p.m.—was 1.6% by weight.

The two bleeding tests gave the following results:
Initial sodium heparin:
Tail transection : 412 (+87% with respect to saline)
Template : 220 (+115% with respect to saline)
Heparin purified by diafiltration:
Tail trasaction : 420 (+90% with respect to saline)
Template : 110 (+7% with respect to saline)

Residue of lyophilized product of the diffusate: no different effect from the effect induced by the saline administration. To all the data reported above, the same comments made for the corresponding data of example 1 apply. Similar results have been obtained using polyacetate, teflon or polysulphone membrane having a cut-off of 1.000 D.

EXAMPLE 3

A 10% solution of sodium heparin obtained as described in example 2, was submitted to the 600 D membrane diafiltration process above described. The heparin solution was added with $CaCl_2$ in a weight ratio of 1:1.5 (Hep: $CaCl_2$).

Figure 6:
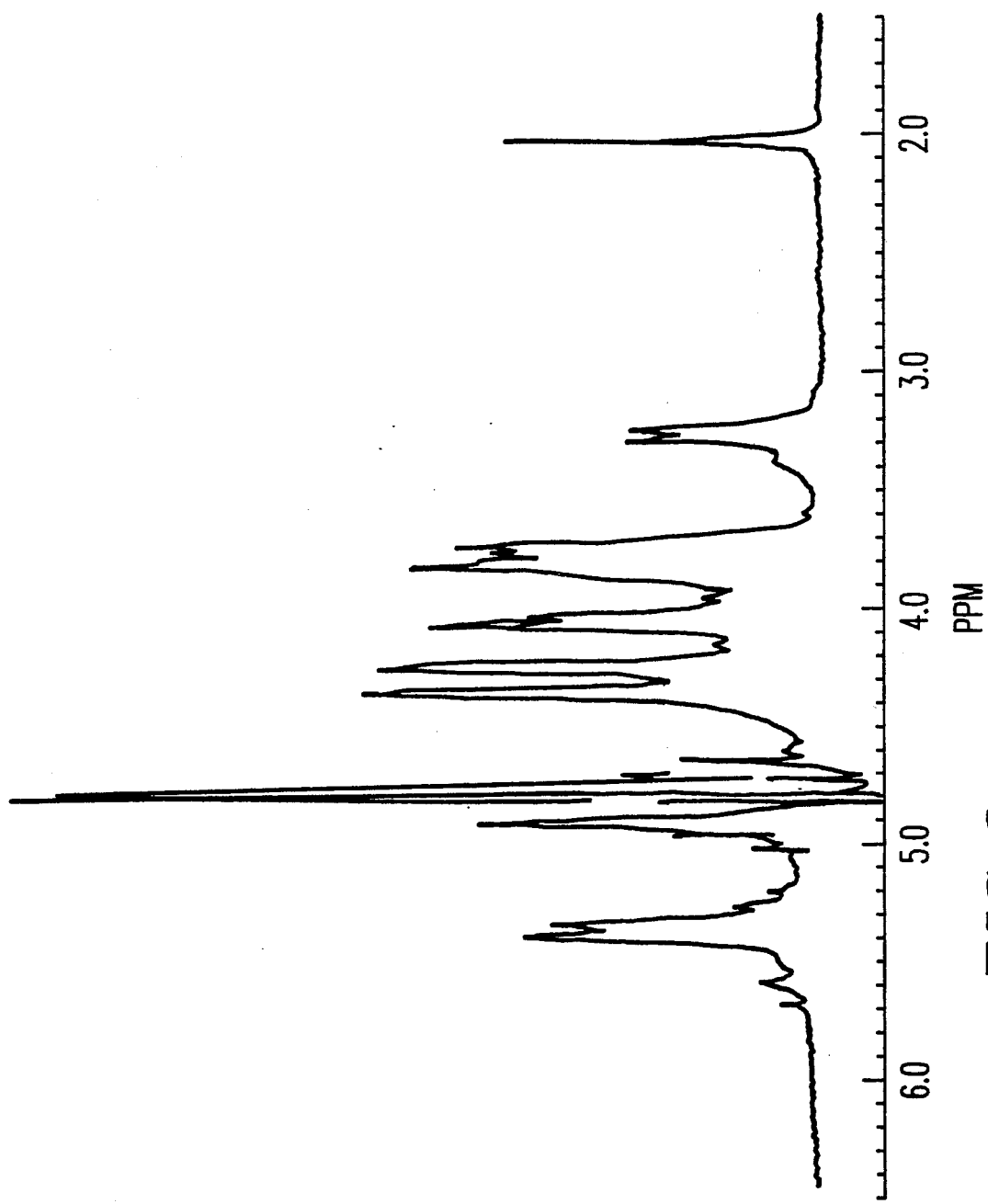

Diafiltration was continued at a constant volume, until almost complete removal of sodium in the diffusate. Calcium heparin, virtually devoid of sodium, was recovered from the solution by lyophilization and, after drying, had the $^1$H—NMR spectrum reported in FIG. 6, wherein the signals at 2.61-3.16-3.18 p.p.m. are absent; these signals are typical of calcium EDTA (of course, sodium EDTA signals are not present both due to the absence of EDTA and because sodium is virtually absent).

From the biologic point of view, both anticoagulant activity and the bleeding data in the two tests are similar to what described in example 2, for the sodium heparin purified by diafiltration.

EXAMPLE 4

Figure 7:
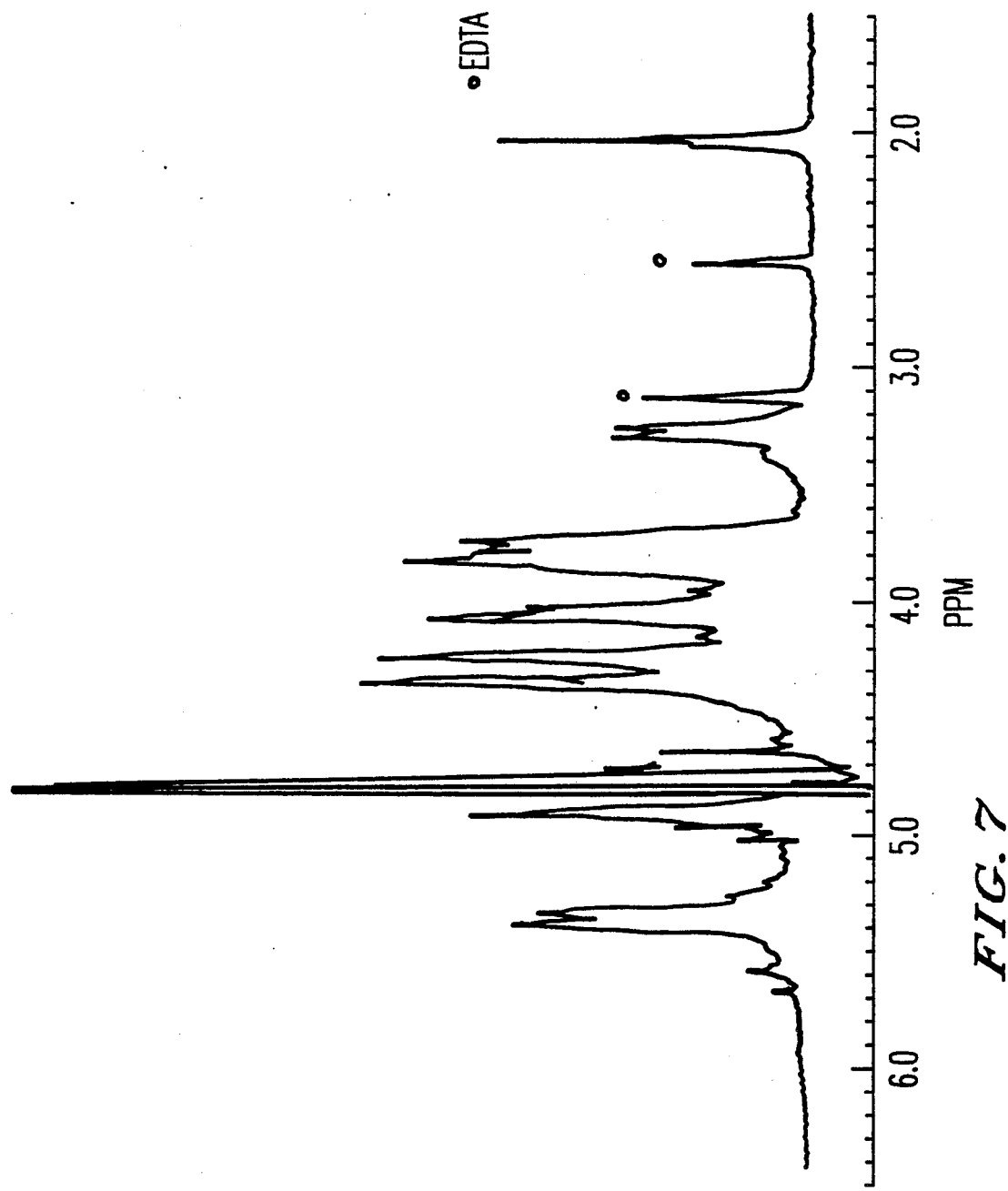

A 10% solution (w/v) of calcium heparin, characterized by the $^1$H—NMR spectrum reported in FIG. 7, wherein the signals at 2.61 and 3.17 p.p.m. are evident, with an EDTA content of 2.1% (calculated as described above), and with an anticoagulant activity of 172 U.I./mg, was added with NaCl until it became 0.5 M in NaCl (in other tests, molarities ranging from 0.1 to 1 M were used). This solution was subsequently diafiltered on 600 D membrane in the same way as described in example 2, but using a NaCl solution having the same molarity. The operation continued until disappearance, in the $^1$H—NMR spectrum, of the EDTA signals of heparin solution samples taken subsequently.

The solution was then diafiltered against water until removal of NaCl, added with $CaCl_2$ and processed as described in example 3. The final calcium heparin (recovery >85%) had an $^1$H—NMR spectrum similar to the one reported in FIG. 6, and an anticoagulant activity of 170 U.I./mg.

The two bleeding tests gave the following data:
Initial calcium heparin:
Tail transection: 440 (+100% with respect to saline)
Template : 255 (+150%)
Purified calcium heparin:
Tail transection: 435 (+97% with respect to saline)
Template : 107 (+4%)

Also for this case, see comments reported in example 1.

EXAMPLE 5

Figure 8:
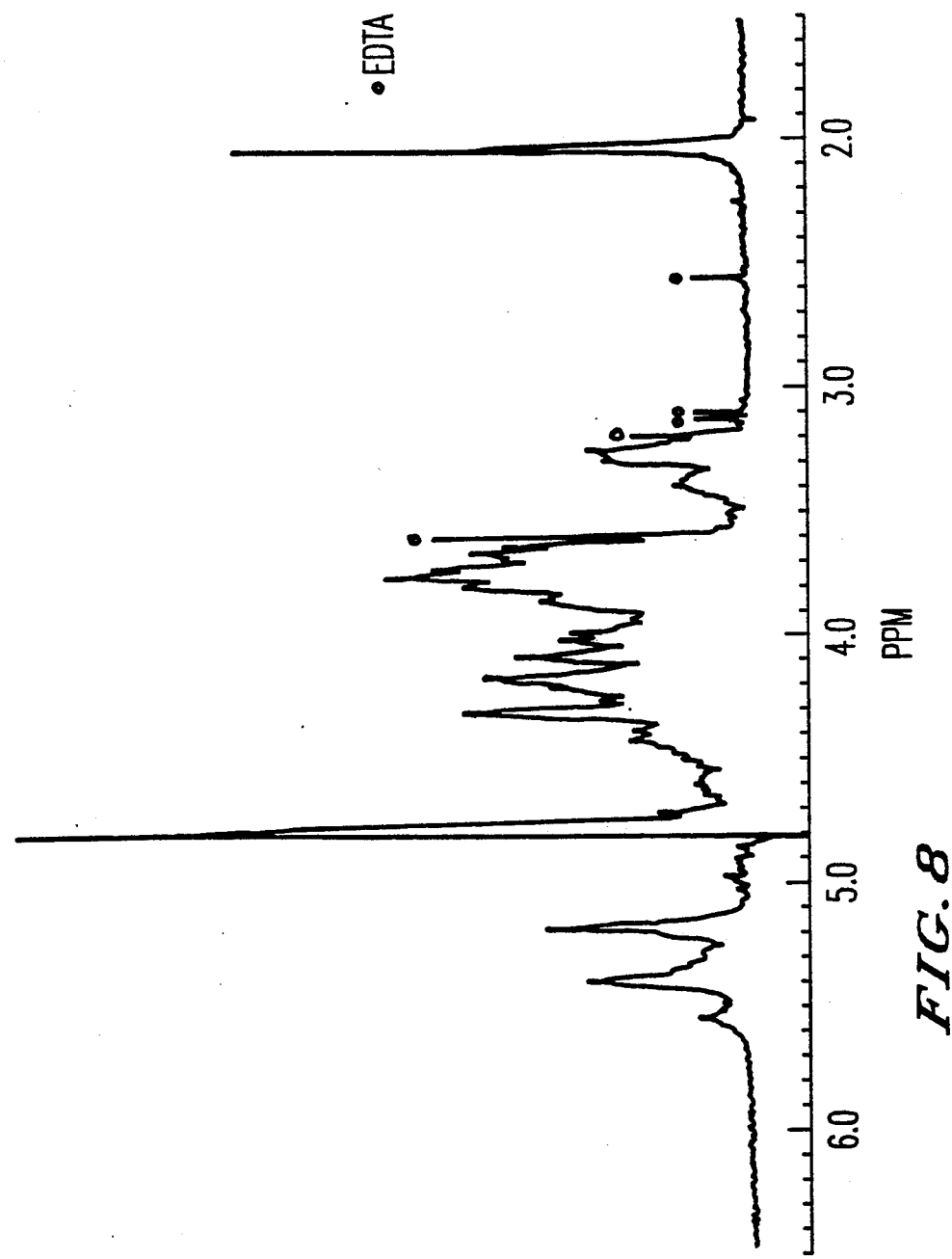

A sample of commercial sodium heparin, of different origin from those used in the previous examples, characterized by an $^1$H—NMR spectrum reported in FIG. 8, and with a total EDTA content equal to 3.0% was processed as described in example 2, keeping constant the volume with a 7% (w/v)NaCl solution. At the end of the process, NaCl was removed by diafiltration against water, and sodium heparin was recovered by precipitation with ethyl alcohol. After drying, the product had an $^1$H—NMR spectrum similar to the one reported in FIG. 2.

EXAMPLE 6

A commercial sodium heparin of different origin from the ones previously described, characterized in that it contained few EDTA in calcium form, and much EDTA in sodium form, for a total weight of 2.5%, was purified as described in the previous examples, both by dialysis and by diafiltration against water or sodium chloride. The individual samples, recovering sodium heparin by lyophilization or by precipitation with ethanol, showed $^1$H—N.M.R. spectra similar to the spectrum of FIG. 2.

The sample, processed by dialysis, showed the following data in the bleeding tests:
Tail transection: 420 (+90% with respect to saline)
Template : 111 (+9% with respect to saline)
For these data, see comments on biological data reported for example 1.

EXAMPLE 7

Figure 9:
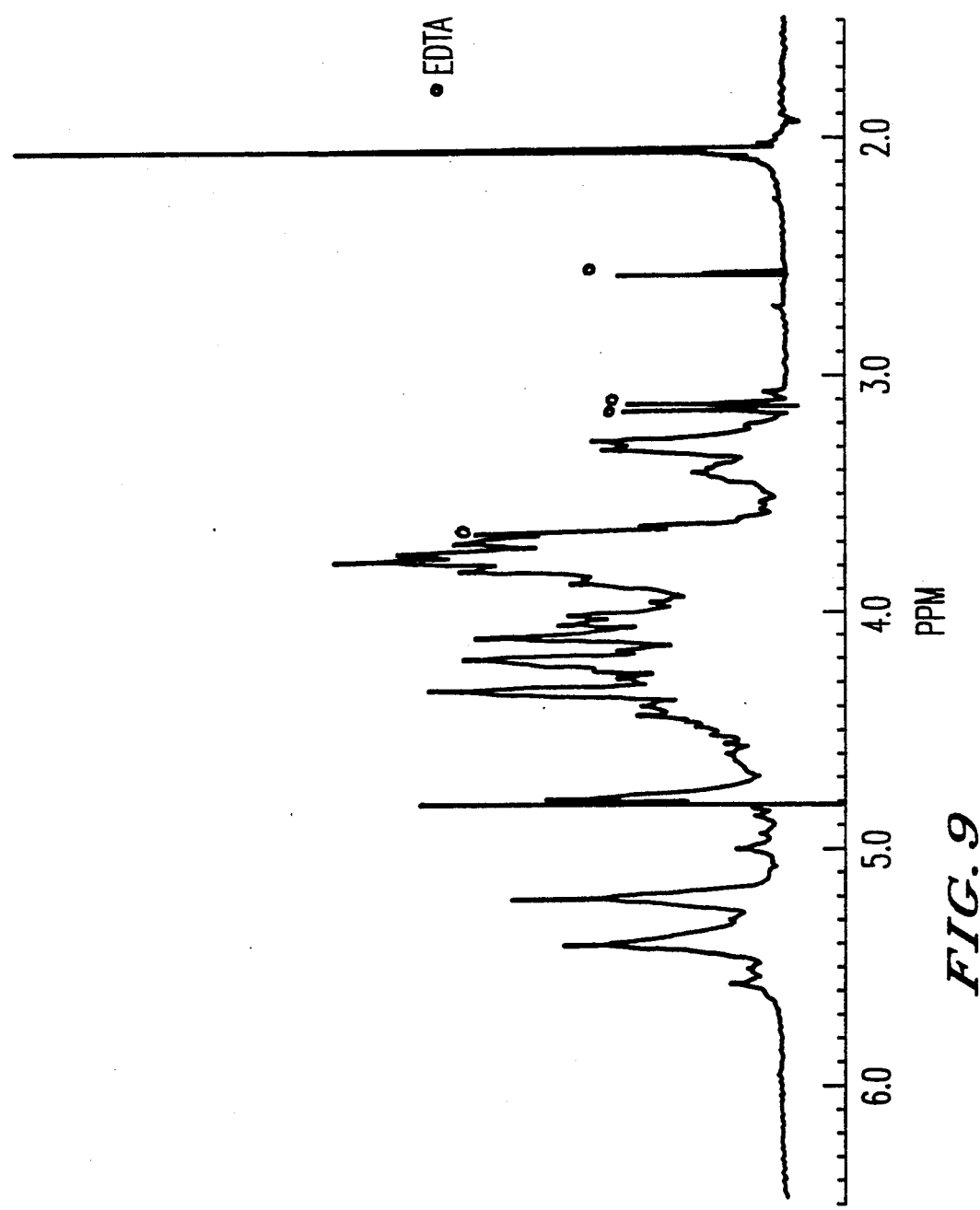

A commercial sodium heparin of different origin form the ones previously described was characterized by the $^1$H—N.M.R. spectrum reported in FIG. 9. In this spectrum various EDTA signals are evident, and in particular the signals concerning the calcium form (signals at 2.62-3.16-3.18 p.p.m.). This fact shows a remarkable presence of calcium as an impurity of sodium heparin. The total content of EDTA was about 1.5% in weight.

Figure 2:
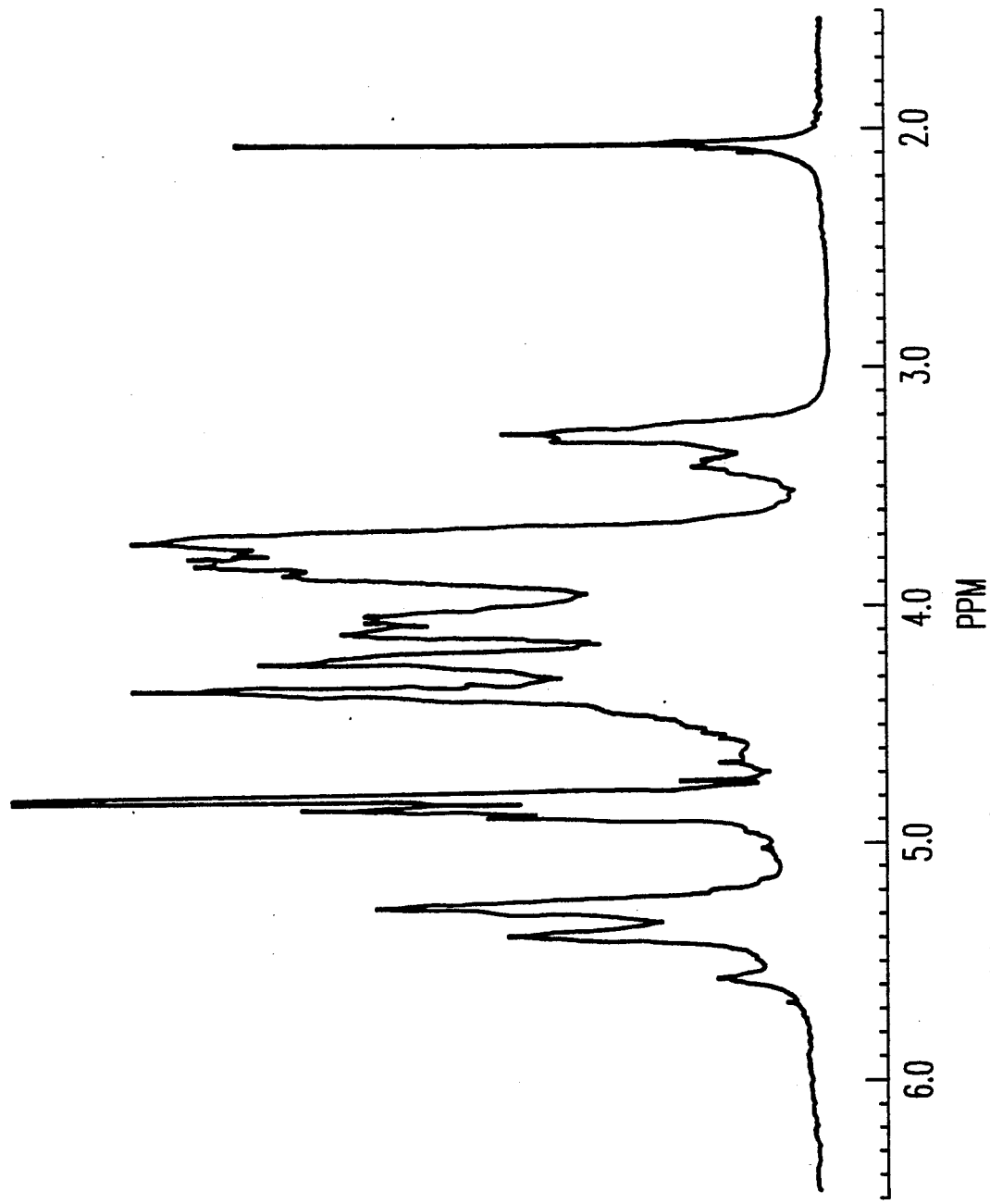

Having been submitted to purification according to the method described in example 2, it gave an heparin devoid of EDTA, as showed by its $^1$H—N.M.R spectrum, completely similar to the one reported in FIG. 2. Moreover, in the template test, the bleeding time, that was 202 seconds for the initial heparin (+98% with respect to saline), decreased to 106 (+3%, non significant, with respect to saline).

EXAMPLE 8

Figure 10:
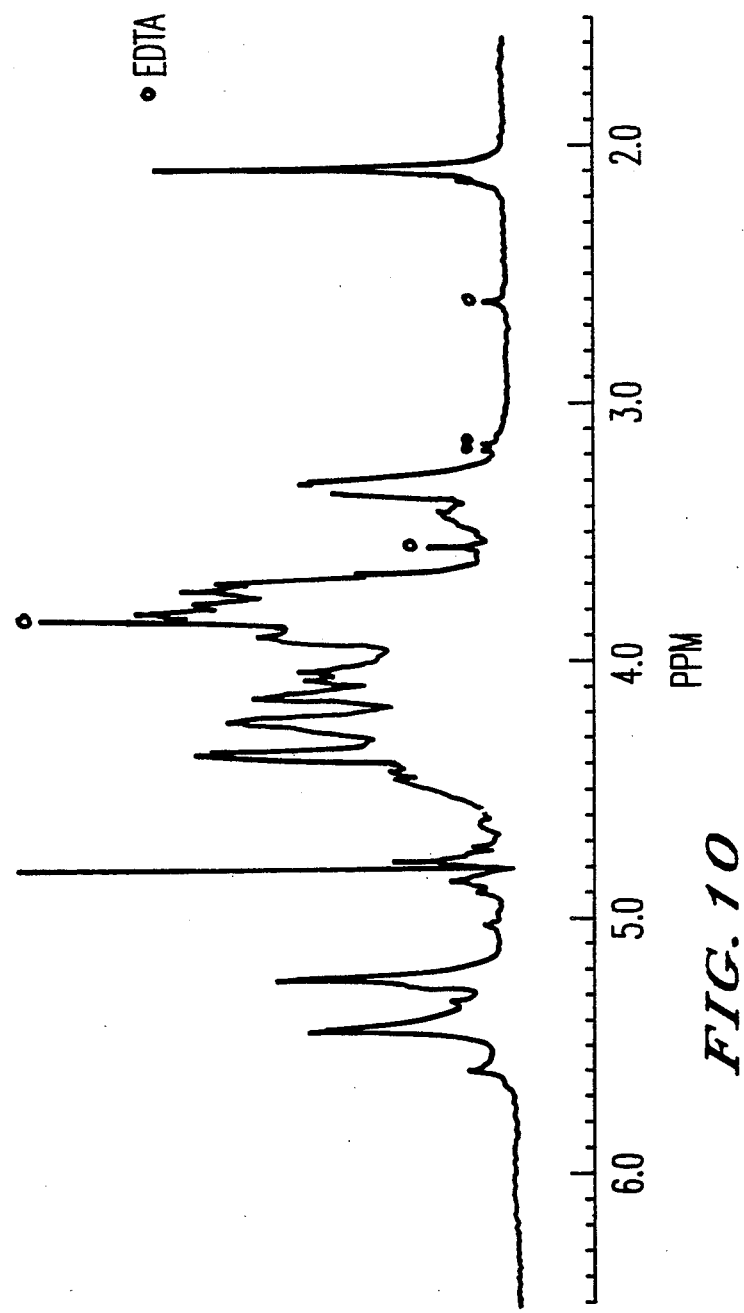

A low molecular weight sodium heparin, average M.W. about 4,000 D, was characterized by an $^1$H—N.M.R spectrum, reported in FIG. 10 (signals at 2.62-3.16-3.18 p.p.m. of calcium EDTA, 3.56 and 3.86 p.p.m. of sodium EDTA; by a total amount of EDTA of 2.5% in weight (calculated on the signal at 2.62 p.p.m., as described above), by an anticoagulant activity of 98 U.I./mg, was submitted, in 2% aqueous solution, to dialysis in a cellulose 600 D cut-off dialysis, against distilled water, for 24 hours.

At the end of this period, the product was recovered by liophylization, and showed an $^1$H—N.M.R. spectrum similar to the one of FIG. 2, wherein the absence of signals attributable to EDTA was evident.

From the biological point of view, the following data were obtained:
initial L.M.W.:
Tail transection: 379 (+72% with respect to
Template : 229 (+124% with respect to saline)
L.M.W. after purification by dialysis:
Tail transection: 396 (+80% with respect to saline)
Template : 115 (+12% with respect to saline)
For the comments on these data, see example 1.

EXAMPLE 9

A low molecular weight heparin sample, from the same batch as the heparin of example 8, was submitted to dialysis in the same conditions mentioned above, but the addition of NaCl until 0.5 M concentration. It was then dialyzed against 0.5 M NaCl for 12 hours, and subsequently against distilled water until elimination of NaCl. The product, recovered by liophylization, had chemico-physical and biological characteristics equal to those of the purified sample according to example 8.

EXAMPLE 10

A low molecular weight heparin sample (average molecular weight 6.000 D) with an $^1$H—N.M.R spectrum in which sodium EDTA signals were particularly evident (3.56 and 3.86 p.p.m.), whereas those of the calcium form were virtually non existant, with an anticoagulant activity of 100 U.I./mg, was submitted to ultrafiltration on 500 D cut-off membrane. The solution volume was periodically restored to the original value, by addition of distilled water. After ultrafiltration of a volume equal to about 5 times the initial volume (in other experiments: volumes from 1 to 10 times), heparin was recovered by lyophilization. In another set of experiments a NaCl 0.5M solution was used instead of distilled water (that is, in other experiments from 0.1 to 1.0 molar); at the end of the experiment, salt was removed by ultrafiltration with addition of water. The products purified in this way were however recovered by lyophilization.

Their $^1$H—N.M.R spectra showed no signals that could be attributed to EDTA, whereas the anticoagulant activity was virtually unchanged.
Bleeding times in the two tests were:
starting L.M.W.:
Tail transection: 497 (+123% with respect to saline)
Template : 2G0 (+86% with respect to saline)
L.M.W. after purification:
Tail transection: 460 (+109% with respect to saline)
Template : 113 (+10% with respect to saline)

EXAMPLE 11

A sample of commercial sodium heparin showing an N.M.R. spectrum in which signals were evident at 3.56 and 3.86 p.p.m. attributed to sodium E.D.T.A. was dissolved into H$_2$O in order to obtain a solution whose concentration ranged from 5 and 15% (w/v). The aqueous solution was added with an equal volume of ethanol in order to obtain the precipitation of heparin. The recovered precipitate was again dissolved in water, in order to obtain a heparin solution whose concentration was about 10%. The solution was treated with the same volume of ethanol in order to obtain a second precipitation of heparin.

The process was repeated for a third time (5 times for other tests) to obtain after the final ethanol precipitation and drying an heparin free from EDTA signals in the NMR spectra.

EXAMPLE 12

A sample of sodium heparin having sulphate/carboxylate ratio of 2.0, average molecular weight 11.500 D and anticoagulant activity 172U.I./mg, showed a $^{13}$C-NMR spectrum wherein the signals between 80 and 86 were present; the two bleeding tests gave the following results:
Tail transection: 453 (+106%)
Template : 254 (+149%)
Same clear solutions, obtained by dissolving the heparin sample in distilled water containing 0.3% of antibacterial phenol sodium salts, having concentrations of 0.5-1.0-5.0-10.0% (w/v), were left to room temperature for different times (from 8 to 48 hours). A white precipitate, which was collected by centrifugation, separated from said solutions; the sodium heparin was recovered from the surnatant clear solution by ethanol addition.

The two solids, after drying under vacuum, were analyzed.

Solid from surnatant
sulphates/carboxylates ratio: 2.0;
average molecular weight : 11.500D;
$^{13}$C—NMR spectrum : absence of signals between 80 and 86 p.p.m; disappearance of the signal at 62.5 p.p.m.; decrease of that at 64 p.p.m.;
anticoagulant activity : 166 U.I./mg
tail transection : 460 (+109%)
template : 117 (+14%).

The deviations versus saline solution were not significant.

Solid from Centrifugation

The $^{13}$C—N.M.R spectrum showed evident signals assigned to heparin (due to sediment contamination by the surnatant), those in the 80–86 p.p.m. region were highly enhanced and both peaks at 62.5 and 64 p.p.m. were present.

The anticoagulant activity was 25 U.I./mg. The bleeding tests gave the following results:
Tail transection: 234 (+6%)
Template : 210 (+106%)

EXAMPLE 13

A sample of commercial sodium heparin (with a sulphate/carboxylate ratio of 2.16, average molecular weight of 15.000 D. and an anticoagulant activity of 176 U.I./mg) showed evident signals attributed to EDTA between 2.50 p.p.m. and 4.00 p.p.m. in the $^1$H—NMR spectrum, like the sample showed in FIG. 1; the bleeding tests showed these values (in seconds):
Tail transection: 423
Template : 235.

These values, compared with the data obtained with the saline solution, showed the following increments:
Tail transection: +94%
Template : +150%.

One part of solid sample was added with 5 or 10 or 15 or 20 or 25 or 30 parts of absolute ethanol; sufficent water was added until 23 or 25 or 28 or 30 percent of water in the system was reached.

The suspension was stirred controlling the temperature at 5° or 10° or 15° or 20° C., over 5 or 15 or 20 minutes.

The resulting suspension was filtered and treated with absolute ethanol to remove the residual water.

The process was repeated 3 or 4 or 5 or 6 or 7 times.

After the final step, the sample was dried with vacuum. The $^1$H—NMR spectrum of the treated sample showed the main signals attributed to heparin. No extra signal attributed to EDTA within 2.5-4.0 p.p.m. region was observed. This spectrum is similar to that in FIG. 2.

Sulphate/Carboxylate ratio: 2.15
Average molecular weight 15.000 D.
Anticoagulant activity 174 U:I:/mg
Bleeding tests (in seconds)
Tail transection : 215
Template : 105

These values, compared with those of the untreated sample, are decreased and the increments with respect to the saline solution are not significant (+110% for the tail transection and +4% for the template). Similar results were obtained using, instead of ethanol, acetone, isopropanol or dioxane.

We claim:

1. A process for the preparation of a composition comprising heparin, heparin fractions, heparin fragments or mixtures thereof, said composition being substantially free of EDTA, comprising:
    subjecting an aqueous solution of heparin, heparin fragments, heparin fractions or mixtures thereof to a series of purification steps comprising dialysis, diafiltrations on membranes having a cut-off valve of from 500-10,000 D, or combinations thereof,
    assaying the resulting preparation so treated for the presence of EDTA, and if EDTA is detected in said preparation, further purifying said preparation by repeating the above steps until said EDTA is removed,
    wherein said assay comprises obtaining the $^1$H—NMR spectrum of the purified preparation of heparin, heparin fractions, heparin fragments, or mixtures thereof and checking said spectrum for the absence of the signals at 2.61, 3.16 and 3.18 ppm and at 3.25 3.64, 3.71 and 3.99 ppm.

2. A process for the preparation of a composition comprising heparin, heparin fractions, heparin fragments or mixtures thereof, said composition being substantially free of EDTA, comprising:
    subjecting an aqueous solution of heparin, heparin fragments, heparin fractions or mixtures thereof to a series of purification steps comprising dialysis, diafiltrations on membranes having a cut-off valve of from 500-10,000 D, or combinations thereof,
    assaying the resulting preparation so treated for the presence of EDTA, and if EDTA is detected in said preparation, further purifying said preparation by repeating the above steps until said EDTA is removed,
    wherein said assay comprises obtaining the $^{13}$C—NMR spectrum of the purified preparation of heparin, heparin fractions, heparin fragments, or mixtures thereof and checking said spectrum for the absence of the signals between 80 and 86 ppm.

* * * * *